United States Patent
Wynn et al.

(10) Patent No.: US 8,168,685 B2
(45) Date of Patent: May 1, 2012

(54) PROCESS FOR THE PRODUCTION OF METHANOL INCLUDING ONE OR MORE MEMBRANE SEPARATION STEPS

(75) Inventors: Nicholas P. Wynn, Redwood City, CA (US); Douglas Gottschlich, Redwood City, CA (US)

(73) Assignee: Membrane Technology and Research, Inc

( * ) Notice: Subject to any disclaimer, the term of this patent is extended or adjusted under 35 U.S.C. 154(b) by 0 days.

(21) Appl. No.: 13/175,399

(22) Filed: Jul. 1, 2011

(65) Prior Publication Data

US 2011/0269854 A1 Nov. 3, 2011

(51) Int. Cl.
   *C07C 27/00* (2006.01)
(52) U.S. Cl. ...................................................... 518/700
(58) Field of Classification Search .................... 518/700
   See application file for complete search history.

(56) References Cited

U.S. PATENT DOCUMENTS

| | | |
|---|---|---|
| 1,569,775 A | 1/1926 | Mittasch et al. |
| 5,034,126 A | 7/1991 | Reddy et al. |
| 7,964,020 B2 | 6/2011 | Baker et al. |
| 2010/0317751 A1* | 12/2010 | Van Brugge et al. ......... 518/726 |
| 2011/0005272 A1 | 1/2011 | Wijmans et al. |

OTHER PUBLICATIONS

Fabrication and Scale-up of PBI-based Membrane System for Pre-Combustion Capture of Carbon Dioxide, K.O'Brien et al, DOE NETL Project Fact Sheet, 2009.
Simultaneous Occurrence of Chemical Grafting, Cross-linking, and Etching on the Surface of Polyimide Membranes and Their Impact on H2/CO2 Separation, B.T. Low et al, Macromolecules, vol. 41, No. 4, pp. 1297-1309, 2008.

* cited by examiner

*Primary Examiner* — Jafar Parsa
(74) *Attorney, Agent, or Firm* — K. Bean; J. Farrant (57) ABSTRACT

Disclosed herein is a methanol production process that includes a membrane separation step or steps. Using the process of the invention, the efficiency of methanol production from syngas is increased by reducing the compression requirements of the process and/or improving the methanol product yield. As an additional advantage, the membrane separation step generates a hydrogen-rich stream which can be sent for other uses. An additional benefit is that the process of the invention may debottleneck existing methanol plants if more syngas or carbon dioxide is available, allowing for feed of imported carbon dioxide into the synthesis loop. This is a way of sequestering carbon dioxide.

20 Claims, 4 Drawing Sheets

PROCESS FOR THE PRODUCTION OF METHANOL INCLUDING ONE OR MORE MEMBRANE SEPARATION STEPS

FIELD OF THE INVENTION

The invention relates to a methanol production process that includes a membrane separation step or steps, using hydrogen-selective membranes, to improve the efficiency of methanol production from natural gas. Hydrogen recovered during the membrane separation step can be sent for other uses. The process of the invention may debottleneck existing methanol plants, allowing for feed of imported carbon dioxide into the synthesis loop, resulting in sequestration of the carbon dioxide and production of additional methanol.

BACKGROUND OF THE INVENTION

Methanol, the simplest alcohol, with a chemical formula of $CH_3OH$, is a light, volatile, colorless, flammable liquid. A polar liquid at room temperature, methanol finds use as an antifreeze, solvent, fuel, and as a denaturant for ethanol. It is also used for producing biodiesel via a transesterification reaction.

The largest use of methanol, however, is in the manufacture of other chemicals. About forty percent of methanol is converted to formaldehyde, and from there into products as diverse as plastics, plywood, paints, explosives, and permanent-press textiles.

Methanol is also used on a limited basis as fuel for internal combustion engines. The use of methanol as a motor fuel received attention during the oil crises of the 1970's due to its availability, low cost, and environmental benefits. However, due to the rising cost of methanol and its corrosivity to rubber and many synthetic polymers used in the auto industry, by the late 1990's automakers had stopped building vehicles capable of operating on either methanol or gasoline ("flexible fuel vehicles"), switching their attention instead to ethanol-fueled vehicles. Even so, pure methanol is required as fuel by various auto, truck, and motorcycle racing organizations.

In 1923, German chemists Alwin Mittasch and Mathias Pier, working for BASF, developed a process for converting synthesis gas (a mixture of carbon monoxide, carbon dioxide, and hydrogen) into methanol. The process used a chromium and magnesium oxide catalyst and required extremely vigorous conditions—pressures ranging from 50 to 220 bar, and temperatures up to 450° C. A patent (U.S. Pat. No. 1,569,775) covering this process was issued on Jan. 12, 1926.

Modern methanol production has been made more efficient through the use of catalysts (typically copper) capable of operating at lower pressures. The modern low-pressure methanol (LPM) production process was developed by ICI in the late 1960's, with the technology now owned by Johnson Matthey (London), a leading licensor of methanol technology.

The production of synthesis gas ("syngas") via steam reforming of natural gas is the first step in many processes for methanol production. At low to moderate pressures and at high temperatures around 850° C., methane reacts with steam on a nickel catalyst to produce syngas according to the following reactions:

$CH_4+H_2O \rightarrow CO+3H_2$ $CO+H_2O \rightarrow CO_2+H_2$

This reaction, commonly referred to as "steam methane reforming" (SMR) is highly endothermic, and maintaining reaction temperature by external heating is a critical part of the process.

The syngas is then compressed and reacted on a second catalyst to produce methanol. Today, the most commonly used catalyst is a mixture of copper, zinc oxide, and alumina first used by ICI in 1966. At 50-100 bar and 250° C., it can catalyze the production of methanol from syngas with high selectivity:

$CO+2H_2 \rightarrow CH_3OH$ $CO_2+3H_2 \rightarrow CH_3OH+H_2O$

The production of syngas from methane produces 3 moles of hydrogen gas for every mole of carbon monoxide (and 4 moles of hydrogen per mole of carbon dioxide), while the methanol synthesis reaction consumes only 2 moles of hydrogen gas per mole of carbon monoxide (and 3 moles of hydrogen gas per mole of carbon dioxide). In both reaction pathways, one more mole of hydrogen is generated than is needed for methanol synthesis. This excess hydrogen occupies capacity in both the compressor train and the methanol reactor. As a result, the methanol production process is inefficient, resulting in unnecessary costs due to increased compressor power requirements and less than optimum methanol yields. Reactants are lost when excess hydrogen is purged from the synthesis loop and used as fuel for the reformer.

Figure 1:
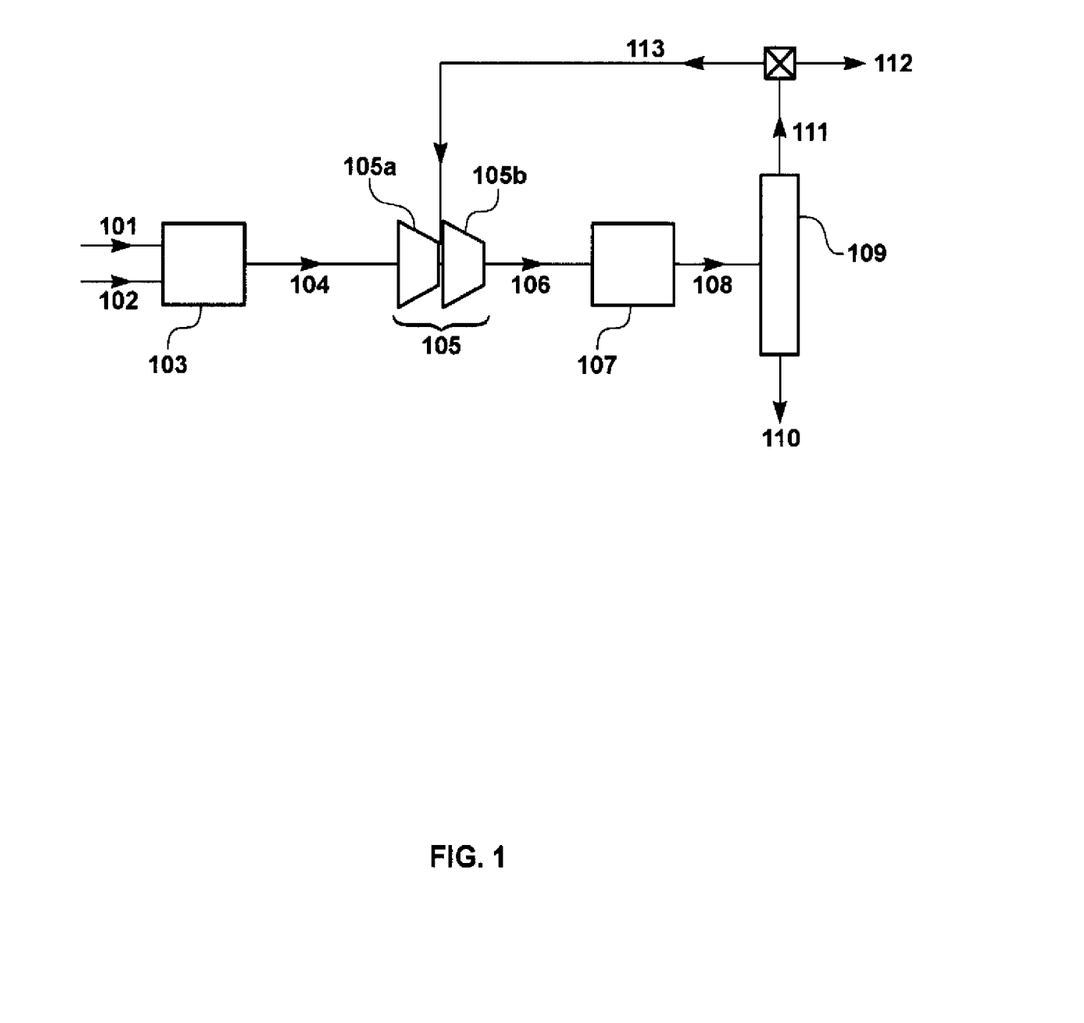
FIG. 1 is a schematic drawing of a conventional methanol production process (not in accordance with the invention).

FIG. 1 is a schematic showing a conventional process for methanol production. Feed streams of natural gas 101 and steam 102 are fed into reformer 103, resulting in the production of syngas stream 104. Syngas stream 104 is then passed to compression chain 105 (typically comprising at least make-up compressor 105a and recycle compressor 105b) to produce high-pressure gas stream 106. High-pressure stream 106 is then passed to methanol synthesis reactor 107 to produce reaction product stream 108, containing methanol and unreacted syngas. This stream 108 is then routed to condenser 109, from which condensed stream 110, containing methanol and water, drops out. Overhead stream 111, containing unreacted syngas and enriched in hydrogen and inerts (methane and possibly nitrogen), is then split into purge stream 112 and recycle stream 113, which is routed back to the recycle compressor 105b, where it is combined with fresh feed.

It would be desirable to have an improved methanol process that is more efficient, with reduced compressor power requirements and/or improved methanol product yield.

SUMMARY OF THE INVENTION

Embodiments of the invention pertain to an improved process for production of methanol from syngas. In particular, embodiments of the invention utilize a membrane separation process to remove excess hydrogen from the syngas before it reaches the methanol synthesis loop. In particular, the membranes used in the separation process exhibit a selectivity for hydrogen over carbon dioxide of at least about 5; preferably, at least about 10; and, more preferably, at least about 15. In addition, the membranes should exhibit a selectivity for hydrogen over carbon monoxide of at least about 20.

Accordingly, disclosed herein is a methanol production process including the following steps:

(a) providing a source of syngas, wherein the syngas has a first composition parameter $R_1$, where $R_1 > 2$;

(b) providing a membrane having a feed side and a permeate side, where the membrane exhibits a selectivity to hydrogen over carbon dioxide of at least about 5, and a selectivity to hydrogen over carbon monoxide of at least about 20;

(c) passing syngas across the feed side;
(d) withdrawing from the permeate side a hydrogen-rich permeate stream, wherein the permeate stream has a second composition parameter $R_2$, where $R_2 > R_1$;
(e) withdrawing from the feed side a hydrogen-depleted residue stream;
(f) compressing the residue stream; and
(g) passing the compressed residue stream to a methanol synthesis loop.

Any membrane that exhibits a selectivity to hydrogen over carbon dioxide of at least about 5, and to hydrogen over carbon monoxide of at least about 20, may be used. Membrane operating temperature is typically within the range of about 50° C. to about 150° C.; preferably, within the range of about 100° C. to about 150° C. Preferred membrane materials include polymers, such as polyimides, polyamides, polyurethanes, polyureas, polybenzimidazoles, and polybenzoxazoles; metals, such as palladium; zeolites; and carbon, by way of example and not by way of limitation.

The feed side of the membrane is typically maintained at a pressure within the range of about 10 bar to about 30 bar, with the permeate side typically maintained at a pressure within the range of about 2 bar to about 5 bar.

The process may further comprise combining the residue stream with an additional gas stream prior to passing the residue stream to the methanol synthesis loop. The additional gas stream has a third composition parameter $R_3$, where $R_3 < R_2$. The additional gas stream may come from additional reformed hydrocarbon (in which case it can be added to the membrane feed), or it may be a carbon dioxide-enriched purge gas from the methanol synthesis loop, or it may be a carbon dioxide-rich stream recovered from an external process, including combustion processes. This stream should not contain a significant amount of inerts, such as methane and nitrogen, which have to be purged from the methanol synthesis loop.

The membrane residue stream—optionally in combination with an additional gas stream—is typically compressed to a pressure within the range of about 45 bar to about 100 bar before being passed to the methanol synthesis loop (which typically consists of at least a recycle compressor, methanol synthesis reactor, product condenser, and purge). The product methanol stream from the synthesis loop is withdrawn from the product condenser.

The overhead stream from the condenser contains unreacted syngas (i.e., hydrogen, carbon monoxide, and carbon dioxide), methane, excess hydrogen, and possibly nitrogen. Most of the overhead stream is combined with fresh feed in the recycle compressor and recycled to the synthesis loop. However, to restrict the build-up in concentration of certain components (namely, methane, excess hydrogen, and possibly nitrogen), a portion of the overhead stream is purged.

By practicing the process of the invention, compression requirements for the process may be reduced by up to 15% or more. Additionally, the process of the invention may debottleneck existing methanol plants if more syngas or carbon dioxide is available. Debottlenecking the compressor allows feed of imported carbon dioxide into the synthesis loop, resulting in additional methanol production, without the drawbacks of feeding carbon dioxide to the reformer. This is a way of sequestering carbon dioxide, thereby preventing its release to the environment. In addition, the process of the invention generates a hydrogen-rich stream from the membrane separation step. This hydrogen-rich stream can be used for other purposes.

A particularly preferred embodiment of the methanol production process of the invention comprises the following steps:
(a) providing a source of syngas, wherein the syngas has a first composition parameter $R_1$, where $R_1 > 2$;
(b) providing a first membrane having a first feed side and a first permeate side, where the first membrane exhibits a selectivity to hydrogen over carbon dioxide of at least about 5, and a selectivity to hydrogen over carbon monoxide of at least about 20;
(c) passing syngas across the first feed side;
(d) withdrawing from the first permeate side a hydrogen-rich first permeate stream, wherein the first permeate stream has a second composition parameter $R_2$, where $R_2 < R_1$;
(e) withdrawing from the first feed side a hydrogen-depleted first residue stream;
(f) compressing the first residue stream;
(g) passing the compressed first residue stream to a methanol synthesis loop to produce a condensed methanol product stream;
(h) withdrawing a purge stream from the methanol synthesis loop to limit the concentration of inerts and excess hydrogen;
(i) treating the purge stream to decrease its R value and its content of methane and nitrogen, whereby the treated purge stream has a third composition parameter $R_3$, where $R_3 < R_2$; and
(j) passing the treated purge stream to the methanol synthesis loop.

The first feed side is typically maintained at a pressure within the range of about 10 bar to about 30 bar, while the first permeate side is maintained at a pressure within the range of about 2 bar to about 5 bar. Membrane operating temperature is typically within the range of about 50° C. to about 150° C.; preferably, within the range of about 100° C. to about 150° C. The first residue stream is typically compressed to a pressure within the range of about 45 bar to about 100 bar before being passed to step (g).

In a preferred embodiment, the purge stream treatment step (i) is a membrane separation process comprising the following steps:
(I) providing a second membrane having a second feed side and a second permeate side, where the second membrane is selective for carbon dioxide over hydrogen and methane;
(II) passing the purge stream across the second feed side;
(III) withdrawing from the second permeate side a carbon dioxide-enriched second permeate stream; and
(IV) passing the second permeate stream as the treated purge stream to step (j).

The second membrane typically has a selectivity for carbon dioxide over hydrogen of at least about 5, and over methane of at least about 10.

DETAILED DESCRIPTION OF THE INVENTION

The terms "natural gas" and "methane" are used interchangeably herein.

Gas percentages given herein are by volume unless stated otherwise.

Pressures as given herein are in bar absolute unless stated otherwise.

For any gas stream herein, the composition may be expressed in terms of a composition parameter, R, where:

$$R = \frac{(\text{molar flow of } H_2 - \text{molar flow of } CO_2)}{(\text{molar flow of } CO + \text{molar flow of } CO_2)},$$

Specific composition parameters are referred to herein as $R_1$, $R_2$, and $R_3$.

Figure 2:
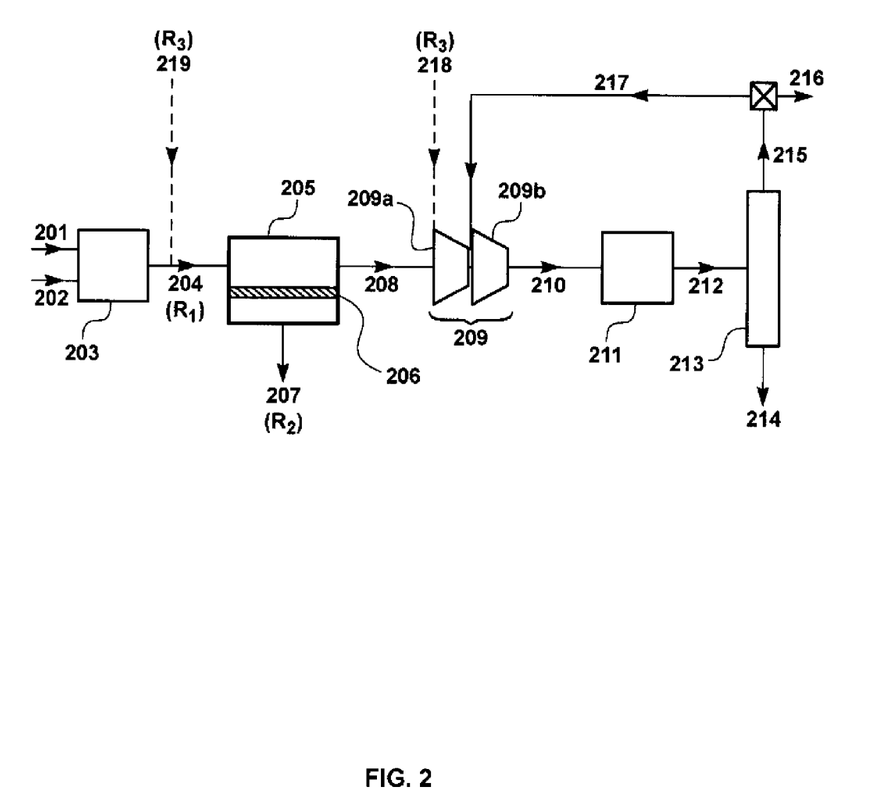
FIG. 2 is a schematic drawing of an embodiment process of the invention for methanol production that involves a membrane separation step.

A schematic drawing of a preferred embodiment process of the invention for methanol production is shown in FIG. 2. Referring to the figure, feed streams of natural gas 201 and steam 202 are fed into, for example, steam reformer 203, resulting in the production of syngas 204. Although FIG. 2 illustrates an example in which syngas is produced using a steam methane reforming process, any source of syngas can be used to provide syngas for use in the process of the invention.

The invention is particularly designed for syngas sources having an excess of hydrogen for methanol production. Expressed quantitatively, the invention is particularly directed to the manufacture of methanol from syngas having a composition parameter, $R_1$, that is greater than 2; that is, $R=R_1>2$.

In accordance with the present invention, the syngas 204 is then passed as a feed stream to a membrane unit 205. Membrane unit 205 includes membranes 206 that exhibit a selectivity to hydrogen over carbon dioxide of at least about 5; preferably, at least about 10; more preferably, at least about 15. In addition, the membranes 206 should exhibit a selectivity for hydrogen over carbon monoxide of at least about 20. Membrane operating temperature is typically within the range of about 50° C. to about 150° C.; preferably, within the range of about 100° C. to about 150° C.

Any membrane with suitable performance properties may be used. Examples of such membranes include the polybenzimidazole (PBI) based membranes taught by K. O'Brien et al. in "Fabrication and Scale-Up of PBI-based Membrane System for Pre-Combustion Capture of Carbon Dioxide" (DOE NETL Project Fact Sheet 2009) and polyimide-based membranes taught by B. T. Low et al. in "Simultaneous Occurrence of Chemical Grafting, Cross-linking, and Etching on the Surface of Polyimide Membranes and Their Impact on $H_2/CO_2$ Separation" (*Macromolecules*, Vol. 41, No. 4, pp. 1297-1309, 2008).

Preferred membrane materials include polymers, such as polyimides, polyamides, polyurethanes, polyureas, polybenzimidazoles, and polybenzoxazoles; metals, such as palladium; zeolites; and carbon, by way of example and not by way of limitation.

The membrane may take the form of a homogeneous film, an integral asymmetric membrane, a multilayer composite membrane, a membrane incorporating a gel or liquid layer or particulates, or any other form known in the art.

The membranes may be manufactured as flat sheets or as fibers and housed in any convenient module form, including spiral-wound modules, plate-and-frame modules, and potted hollow-fiber modules. The making of all these types of membranes and modules is well-known in the art.

Flat-sheet membranes in spiral-wound modules is the most preferred choice for the membrane/module configuration. A number of designs that enable spiral-wound modules to be used in counterflow mode, with or without sweep on the permeate side, have been devised. A representative example is described in U.S. Pat. No. 5,034,126, to Dow Chemical.

Membrane unit 205 may contain a single membrane module or bank of membrane modules or an array of modules. A single unit or stage containing one or a bank of membrane modules is adequate for many applications. If the residue stream requires further hydrogen removal, it may be passed to a second bank of membrane modules for a second processing step. If the permeate stream requires further concentration, it may be passed to a second bank of membrane modules for a second-stage treatment. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

Referring back to FIG. 2, the syngas 204 is passed across the feed side of the membranes 206, typically at a temperature within the range of about 50° C. to about 150° C.; preferably, within the range of about 100° C. to about 150° C. A permeate stream 207 is withdrawn from the permeate side. Permeate stream 207 is enriched in hydrogen as compared with syngas stream 204, and has a composition parameter $R_2$, where $R_2>R_1$. Hydrogen-rich permeate stream 207 can be used for other purposes, as desired.

The feed side of the membrane is typically maintained at a pressure within the range of about 10 bar to about 30 bar, with the permeate side typically maintained at a pressure within the range of about 2 bar to about 5 bar.

A hydrogen-depleted residue stream 208 is withdrawn from the feed side of membrane unit 205. Residue stream 208 is then routed to make-up compressor 209a, where it is compressed to a pressure within the range of about 45 bar to about 100 bar. Residue stream 208 can optionally be combined with an additional gas stream, 218, prior to passing to make-up compressor 209a (which is part of compressor train 209).

Additional gas stream 218 has a composition parameter $R_3$, where $R_3<R_2$. The addition of gas stream 218 to the process results in additional methanol production. Additional gas stream 218 may come from additional carbon dioxide imported from a local source. For example, and not by way of limitation, the additional carbon dioxide may come from a chemical process such as ethylene oxide production.

Alternatively, additional carbon dioxide may be imported from treated combustion exhaust gases generated by a coal-fired or natural gas-fired power plant, as described, for example, in commonly owned U.S. Pat. No. 7,964,020, and copending U.S. application Ser. Nos. 12/807,846; 13/122,136; 13/123,342; and 13/123,364. This is a way of sequestering carbon dioxide.

The additional gas stream may alternatively come from additional reformed hydrocarbon, in which case, the additional gas 219 is introduced into the process before the membrane step.

High-pressure stream 210—which comprises residue stream 208, optionally in combination with additional gas stream 218—is passed to methanol synthesis reactor 211, to produce reaction product stream 212, containing methanol and unreacted syngas.

Methanol synthesis reactors are known in the art and typically rely on a catalyst bed to catalyze the reaction of carbon oxides and hydrogen to produce methanol. As discussed in the Background of the Invention, the most common catalyst in use today is a mixture of copper, zinc oxide, and alumina first used by ICI in 1966. At 50-100 bar and 250° C., it can catalyze the production of methanol from carbon oxides and hydrogen with high selectivity.

Referring back to FIG. 2, reaction product stream 212 is then routed to condenser 213, from which condensed product stream 214, containing approximately 75% methanol and 25% water, drops out. Overhead stream 215, containing unreacted syngas (i.e., hydrogen, carbon monoxide, and carbon dioxide), methane, excess hydrogen, and possibly nitrogen, is withdrawn from the condenser. At least a portion of the overhead stream 215 is routed as a recycle stream 217 back to the recycle compressor 209b, where it is combined with fresh feed. To restrict the build-up in concentration of certain components (namely, methane, excess hydrogen, and possibly nitrogen), a portion 216 of the overhead stream is purged.

As discussed above, the membrane separation step generates a hydrogen-rich stream which can be used for whatever purpose is desired. Furthermore, because hydrogen is withdrawn in the membrane separation step, the amount of gas that is routed through the compression chain is less than with the conventional process, thereby lowering the compression requirements of the process. Also as a result, the hydrogen content of the condenser overhead stream is lower, so that more of the overhead stream can be recycled back to the recycle compressor 209b (rather than purged), resulting in less gas wastage.

Figure 3:
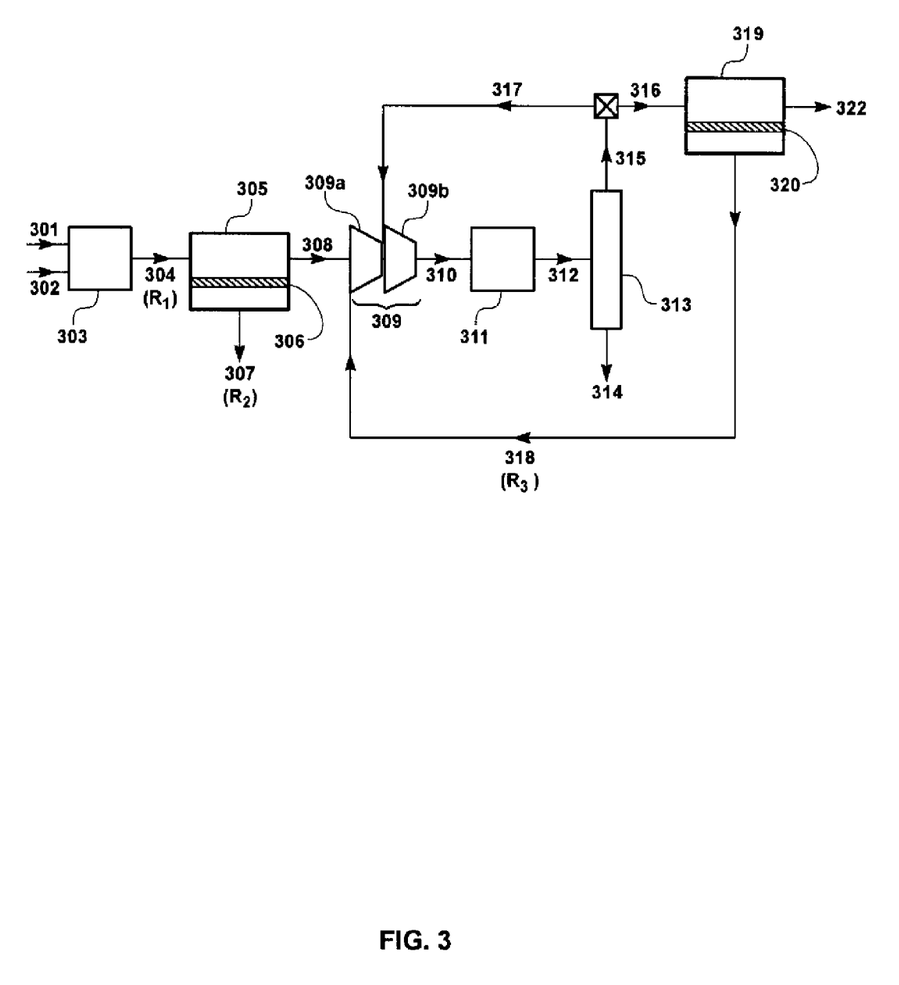
FIG. 3 is a schematic drawing of a particularly preferred embodiment process of the process of the invention that involves two membrane separation steps.

A particularly preferred embodiment of the invention, which involves two membrane separation steps, is illustrated schematically in FIG. 3. Referring to the figure, feed streams of natural gas 301 and steam 302 are fed into, for example, steam reformer 303, resulting in the production of syngas 304, which has a composition parameter $R_1$ (as described above with respect to the process embodiment shown in FIG. 2). Although FIG. 3 illustrates an example in which syngas is produced using a steam methane reforming process, any source of syngas can be used to provide syngas for use in the process of the invention, provided that the syngas has a composition parameter $R_1 > 2$.

The syngas 304 is passed as a feed stream to a first membrane unit 305. First membrane unit 305 includes membranes 306 that are selective to hydrogen over carbon oxides, and exhibit the membrane properties discussed above with respect to the process embodiment shown in FIG. 2.

The syngas 304 is passed across the feed side of the membranes 306, typically at a temperature within the range of about 50° C. to about 150° C.; preferably, within the range of about 100° C. to about 150° C. A first permeate stream 307 is withdrawn from the permeate side. First permeate stream 307 is enriched in hydrogen as compared with syngas stream 304, and has a composition parameter $R_2$, where $R_2 > R_1$. Hydrogen-rich first permeate stream 307 can be used for other purposes, as desired.

A hydrogen-depleted first residue stream 308 is withdrawn from the feed side of first membrane unit 305. First residue stream 308 is then routed to make-up compressor 309a, where it is compressed to a pressure within the range of about 30 bar to about 100 bar. First residue stream 308 can optionally be combined with an additional gas stream, 318, prior to passing to make-up compressor 309a (which is part of compressor train 309). Additional gas stream 318 has a composition parameter $R_3$, where $R_3 < R_2$. In this embodiment, additional gas stream 318 is the permeate stream from the second permeate step, which will be discussed in detail further on.

High-pressure stream 310—which comprises first residue stream 308, in combination with additional gas stream 318—is passed to methanol synthesis reactor 311, to produce reaction product stream 312, containing methanol and unreacted syngas.

Reaction product stream 312 is then routed to condenser 313, from which condensed product stream 314, containing approximately 75% methanol and 25% water, drops out. Overhead stream 315, containing unreacted syngas (i.e., hydrogen, carbon monoxide, and carbon dioxide), methane, excess hydrogen, and possibly nitrogen, is withdrawn from the condenser. At least a portion of the overhead stream 315 is routed as a recycle stream 317 back to the recycle compressor 309b, where it is combined with fresh feed.

To restrict the build-up in concentration of certain components (namely, methane, excess hydrogen, and possibly nitrogen), a portion of the overhead stream is sent as a feed stream 316 to a second membrane separation unit 319 to recover carbon dioxide and purge the other gases. Second membrane separation unit 319 includes membranes 320 that are selective for carbon dioxide over hydrogen, methane, and nitrogen. In particular, the membranes in second unit 319 typically have a selectivity for carbon dioxide over hydrogen of at least about 5; over methane of at least about 10; and, over nitrogen of at least about 20.

A carbon dioxide-enriched second permeate stream 318 is withdrawn from the permeate side of second membrane unit 319. The carbon dioxide content in second permeate stream 318 has now been built up from about 2.5 vol % to about 8 vol %. Second permeate stream 318 represents approximately 25% of the total volume of purge stream 316.

Carbon dioxide-enriched second permeate stream 318 is then combined with first residue stream 308 prior to passing to the methanol synthesis loop. Second permeate stream 318 has a composition parameter $R_3$, where $R_3 < R_2$. The addition of carbon dioxide-enriched second permeate stream 318 to first residue stream 308 results in additional methanol production.

Carbon dioxide-depleted second residue stream 322 is withdrawn from the membrane side of second membrane separation unit 319. This stream can then be sent for use as fuel gas or for any other desired purpose.

The invention is now further described by the following examples, which are intended to be illustrative of the invention, but are not intended to limit the scope or underlying principles in any way.

EXAMPLES

Example 1

Conventional Methanol Production Process (not in Accordance with the Invention)

The computer calculations in the following Examples were performed using a modeling program, ChemCad 5.6 (ChemStations, Inc., Houston, Tex.) containing code developed by assignee's engineering group for applications specific to assignee's processes.

The calculation for this Example was performed using the flow scheme shown in FIG. 1 and described in the Background of the Invention, above. This flow scheme does not include a membrane separation step upstream of the methanol synthesis process (not in accordance with the invention). Syngas flow was assumed to be 106 metric tons per hour (Mt/h).

The flow rates and chemical compositions of the streams in the methanol synthesis loop were calculated. The results of this calculation are shown in Table 1.

TABLE 1

| Parameter/Stream | Syngas 104 | Reactor Feed Gas 106 | Reactor Output 108 | Condensate 110 | Overhead Stream 111 | Purge Gas 112 | Recycle Gas 113 |
| --- | --- | --- | --- | --- | --- | --- | --- |
| Total Flow (Mt/h) | 106 | 185 | 185 | 92.0 | 93.4 | 14.0 | 79.4 |
| Temperature (° C.) | 150 | 65 | 280 | 40 | 40 | 40 | 40 |
| Pressure (bar) | 16 | 100 | 100 | 100 | 100 | 100 | 100 |
| Component (mol %) | | | | | | | |
| Hydrogen | 73.4 | 79.2 | 71.1 | 0.24 | 83.2 | 83.2 | 83.2 |
| Carbon monoxide | 14.9 | 6.6 | 0.80 | 0.01 | 0.93 | 0.93 | 0.93 |
| Carbon dioxide | 7.8 | 3.7 | 0.91 | 0.43 | 0.99 | 0.99 | 0.99 |
| Methane | 3.7 | 9.7 | 11.8 | 0.45 | 13.7 | 13.7 | 13.7 |
| Nitrogen | 0.20 | 0.54 | 0.65 | 0 | 0.76 | 0.76 | 0.76 |
| Methanol | 0 | 0.23 | 11.1 | 74.0 | 0.39 | 0.39 | 0.39 |
| Water | 0 | 0.04 | 3.7 | 24.9 | 0.06 | 0.06 | 0.0 |

In this "no membrane" example, approximately 96.7% of the carbon oxides in the syngas are converted to methanol. Most of the balance, approximately 2.3% of the carbon oxides in the feed syngas, is lost in the purge gas. The make-up compressor compresses 24,000 lbmol/h, with a power consumption of 29,000 HP. The recycle compressor compresses 60,000 lbmol/h, with a power consumption of 6,400 HP.

Example 2

Methanol Production Process in Accordance with the Invention

The calculation for this Example was performed using the flow scheme shown in FIG. 2 and described in the Detailed Description, above. This flow scheme includes a membrane separation step upstream of the methanol synthesis loop.

The membranes, 206, in membrane separation unit, 205, were assumed to have the properties shown in Table 2, at a membrane operating temperature within the range of about 50° C. and about 150° C.

TABLE 2

| Gas | Permeance (gpu)* | $H_2$/Gas Selectivity** |
| --- | --- | --- |
| Hydrogen | 300 | — |
| Carbon monoxide | <2 | >100 |
| Carbon dioxide | 20 | 15 |
| Methane | <2 | >100 |
| Nitrogen | <2 | >100 |
| Water | 500 | 0.6 |

*Gas permeation unit; 1 gpu = $1 \times 10^{-6}$ cm$^3$(STP)/cm$^2 \cdot$ s $\cdot$ cmHg

**Estimated, not measured

As with Example 1, syngas flow for this calculation was assumed to be 106 Mt/h. The flow rates and chemical compositions of the streams in the methanol synthesis loop were calculated. The results of this calculation are shown in Table 3.

TABLE 3

| Parameter/ Stream | Syngas 204 | Membrane Permeate 207 | Treated Syngas 208 | Reactor Feed Gas 210 | Reactor Output 212 | Condensate 214 | Overhead Stream 215 | Purge Gas 216 | Recycle Gas 217 |
| --- | --- | --- | --- | --- | --- | --- | --- | --- | --- |
| Total Flow (Mt/h) | 106 | 4.3 | 102 | 208 | 208 | 92.3 | 116 | 9.3 | 107 |
| Temperature (° C.) | 150 | 150 | 150 | 63 | 280 | 40 | 40 | 40 | 40 |
| Pressure (bar) | 16 | 2 | 16 | 100 | 100 | 100 | 100 | 100 | 100 |
| Component (mol %) | | | | | | | | | |
| Hydrogen | 73.4 | 98.0 | 69.1 | 67.0 | 54.2 | 0.19 | 65.6 | 65.6 | 65.6 |
| Carbon monoxide | 14.9 | 0.88 | 17.4 | 7.6 | 1.0 | 0 | 1.2 | 1.2 | 1.2 |
| Carbon dioxide | 7.8 | 0.91 | 9.0 | 4.3 | 1.1 | 0.50 | 1.2 | 1.2 | 1.2 |
| Methane | 3.7 | 0.22 | 4.3 | 19.6 | 24.7 | 0.96 | 29.7 | 29.7 | 29.7 |
| Nitrogen | 0.20 | 0.01 | 0.23 | 1.1 | 1.4 | 0.01 | 1.7 | 1.7 | 1.7 |
| Methanol | 0 | 0 | 0 | 0.28 | 13.3 | 73.6 | 0.46 | 0.46 | 0.46 |
| Water | 0 | 0 | 0 | 0.04 | 4.4 | 24.7 | 0.07 | 0.07 | 0.07 |

By comparison, in the present "membrane" Example (in accordance with the invention), carbon oxide losses in the purge gas are almost halved (1.1% of the carbon oxides in the feed syngas), because the purge stream is significantly smaller. However, 1.2% of the carbon oxides are lost in the membrane permeate due to co-permeation of carbon oxides with hydrogen. Overall, about 96.7% of the carbon oxides in the syngas are converted to methanol, essentially the same yield as the "no membrane" case.

The benefit of the invention in this example is a significant decrease in compression requirements due to reduced gas flow through the compressor train 209. The make-up compressor 209a compresses 20,400 lbmol/h, with a power consumption of 25,000 HP (a 15% decrease). The recycle compressor 209b compresses 51,000 lbmol/h, with a power consumption of 5,800 HP (a 9% decrease).

Example 3

Methanol Production Loss from Co-Permeation of Carbon Dioxide

Many hydrogen-permeable membranes show good selectivity for hydrogen over carbon monoxide. However, good selectivity for hydrogen over carbon dioxide is much harder to realize. Because of this, a series of calculations of the type described in FIG. 2 was performed, varying the hydrogen/carbon dioxide selectivity from 3 to 15. The results of the calculations were used to create the curves shown in FIG. 4, which is a plot 400 showing methanol production loss (due to co-permeation of carbon oxides) 401 as a function of membrane hydrogen/carbon dioxide selectivity 402. Curve 403 represents a permeate stream pressure of 4 bar (60 psia); curve 404 represents a permeate stream pressure of 2 bar (30 psia). Feed stream pressure in both cases was 240 psia.

Figure 4:
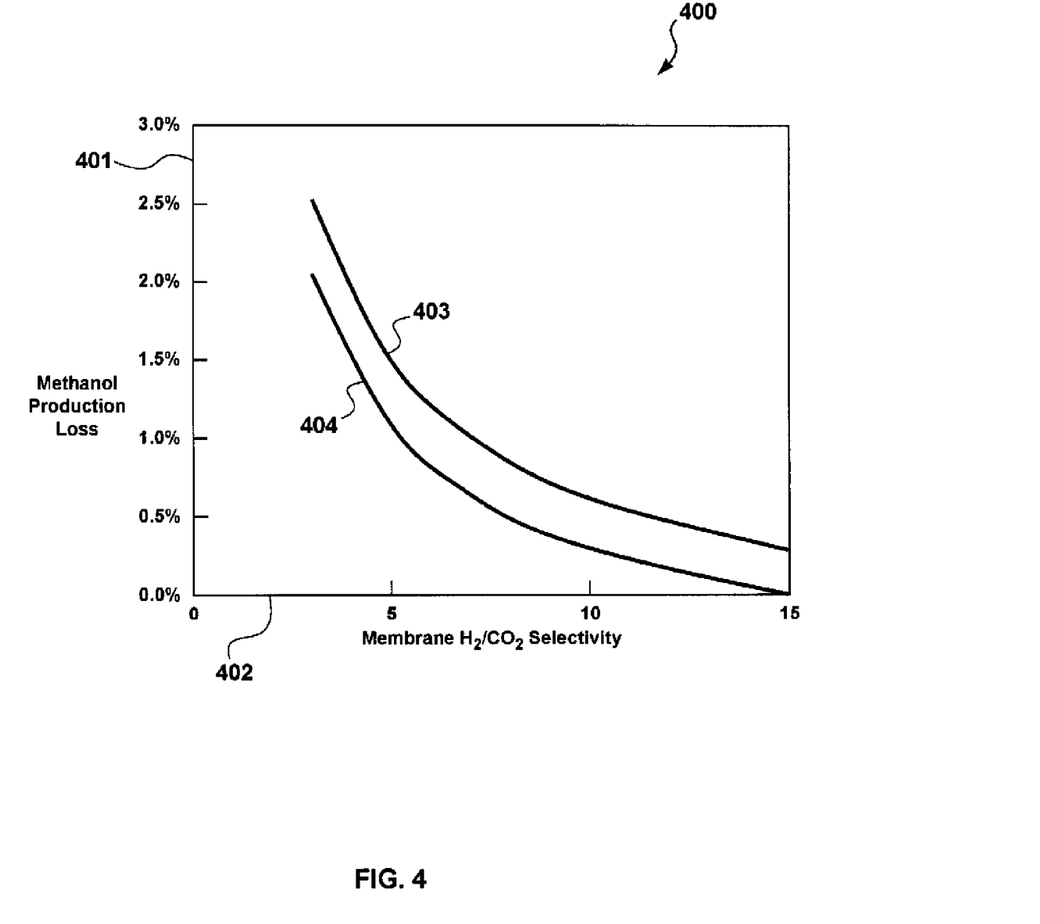
FIG. 4 is a plot showing methanol production loss as a function of membrane hydrogen/carbon dioxide selectivity.

As can be seen from the figure, at a given membrane selectivity, methanol production loss from co-permeation of carbon oxides is slightly higher at a permeate pressure of 4 bar (curve 403) than at 2 bar (curve 404), because the slower permeating carbon oxide components are more affected by changes in the pressure ratio than the faster permeating hydrogen. At a permeate pressure of 4 bar, methanol production loss from co-permeation of carbon oxides drops from approximately 2.5%, at a membrane hydrogen/carbon dioxide selectivity of 4, to only about 0.3% at a selectivity of 15. At a permeate pressure of 2 bar, methanol production loss drops from approximately 2% at a membrane hydrogen/carbon dioxide selectivity of 4, to essentially negligible at a selectivity of 15.

The data shown in FIG. 4 highlight that a hydrogen/carbon dioxide selectivity of at least 10 and, preferably, 15 is necessary to restrict membrane carbon oxide loss—and consequent methanol production loss—so that it does not outweigh the reduction in carbon oxide loss, due to less loop purging being required.

Example 4

Methanol Production Process in Accordance with the Invention

The calculation for this Example was performed using the flow scheme shown in FIG. 3 and described in the Detailed Description, above. This flow scheme includes a membrane separation step upstream of the methanol synthesis loop (unit 305) and a second membrane separation step on the synthesis loop purge gas (unit 319).

The membranes, 306, in membrane separation unit, 305, were assumed to have the properties shown in Table 2, above, at a membrane operating temperature within the range of about 50° C. and about 150° C.

The membranes, 320, in membrane separation unit, 319, were selective for carbon dioxide over hydrogen and were assumed to have the properties shown in Table 4, at a membrane operating temperature within the range of about 0° C. and about 40° C.

TABLE 4

| Gas | Permeance (gpu) * | $CO_2$/Gas Selectivity ** |
|---|---|---|
| Carbon dioxide | 600 | — |
| Hydrogen | 60 | 10 |
| Carbon monoxide | 20 | 30 |
| Methane | 20 | 30 |
| Nitrogen | 30 | 20 |
| Water | 2000 | 0.3 |

* Gas permeation unit; 1 gpu = 1 × 10$^{-6}$ cm$^3$(STP)/cm$^2$ · s · cmHg
** Estimated, not measured As with Example 1, syngas flow for this calculation was assumed to be 106 MT/h. The flow rates and chemical compositions of the streams in the synthesis loop were calculated. The results of this calculation are shown in Table 5.

TABLE 5

| Parameter / Stream | Syngas 304 | First Membrane Permeate 307 | Treated Syngas 308 | Reactor Feed Gas 310 | Reactor Output 312 | Condensate 314 | Recycle Gas 317 | Second Membrane Permeate 318 | Exhaust Gas 322 |
|---|---|---|---|---|---|---|---|---|---|
| Total Flow (Mt/h) | 106 | 4.3 | 102 | 220 | 220 | 93 | 114 | 4.1 | 8.6 |
| Temperature (° C.) | 150 | 150 | 150 | 63 | 280 | 40 | 40 | 40 | 40 |
| Pressure (bar) | 16 | 2 | 16 | 100 | 100 | 100 | 100 | 16 | 100 |
| Component (mol %) | | | | | | | | | |
| Hydrogen | 73.4 | 98.0 | 69.1 | 70.9 | 60.9 | 0.2 | 71.3 | 82.3 | 64.1 |
| Carbon monoxide | 14.9 | 0.9 | 17.4 | 6.5 | 0.8 | 0 | 0.9 | 0.5 | 1.2 |
| Carbon dioxide | 7.8 | 0.9 | 9.0 | 3.8 | 0.9 | 0.4 | 1.0 | 2.3 | 0.2 |
| Methane | 3.7 | 0.2 | 4.3 | 17.5 | 21.3 | 0.8 | 24.8 | 13.1 | 32.6 |
| Nitrogen | 0.2 | 0 | 0.2 | 1.0 | 1.2 | 0 | 1.4 | 0.7 | 1.9 |
| Methanol | 0 | 0 | 0 | 0.3 | 11.2 | 73.6 | 0.4 | 1.0 | 0.1 |
| Water | 0 | 0 | 0 | 0 | 3.7 | 25.0 | 0.1 | 0.2 | 0 |

By comparison with Example 1 (no membrane), in the present "membrane" Example (in accordance with the invention), carbon oxide losses in the purge gas are reduced by 70% (down to 0.65% of the carbon oxides in the feed syngas), because the purge stream is: (a) significantly smaller due to incorporation of the first membrane removing hydrogen from the syngas feed; and (b) lower in carbon dioxide concentration because of the second membrane permeating a carbon dioxide-enriched stream, which is recycled to the methanol synthesis loop. However, 1.2% of the carbon oxides are lost in the first membrane permeate due to co-permeation. Overall, about 97.6% of the carbon oxides in the syngas are converted to methanol—almost 1% more than in the "no membrane" case.

In this Example, the make-up and recycle compressor requirements are similar to those in Example 1 (not in accordance with the invention). In this example, the benefit of the invention is realized by improving methanol yield.

We claim:

1. A process for the production of methanol comprising the following steps:
   (a) providing a source of syngas, wherein the syngas has a first composition parameter $R_1$, and wherein $R_1 > 2$;
   (b) providing a membrane having a feed side and a permeate side, where the membrane exhibits a selectivity to hydrogen over carbon dioxide of at least about 5, and a selectivity to hydrogen over carbon monoxide of at least about 20;
   (c) passing syngas across the feed side;
   (d) withdrawing from the permeate side a hydrogen-rich permeate stream, wherein the permeate stream has a second composition parameter $R_2$, and wherein $R_2 > R_1$;
   (e) withdrawing from the feed side a hydrogen-depleted residue stream;
   (f) compressing the residue stream; and
   (g) passing the compressed residue stream to a methanol synthesis loop.

2. A process in accordance with claim 1, wherein the membrane exhibits a selectivity to hydrogen over carbon dioxide of at least about 10.

3. A process in accordance with claim 1, wherein the syngas is passed across the feed side at a temperature within the range of about 50° C. to about 150° C.

4. A process in accordance with claim 1, wherein the process further comprises combining the residue stream with an additional gas stream prior to passing the residue stream to the methanol synthesis loop, wherein the additional gas stream has a third composition parameter $R_3$, and wherein $R_3 < R_2$.

5. A process in accordance with claim 4, wherein the additional gas stream comes from additional reformed hydrocarbon.

6. A process in accordance with claim 4, wherein the additional gas stream is a carbon dioxide stream recovered from flue gas.

7. A process in accordance with claim 4, wherein the additional gas stream is a carbon dioxide-rich stream recovered from another chemical process.

8. A process in accordance with claim 1, wherein the feed side is maintained at a pressure within the range of about 10 bar to about 30 bar.

9. A process in accordance with claim 1, wherein the permeate side is maintained at a pressure within the range of about 2 bar to about 5 bar.

10. A process in accordance with claim 1, wherein the residue stream is compressed to a pressure within the range of about 45 bar to about 100 bar before being passed to step (g).

11. A process is accordance with claim 1, wherein a product stream from the methanol synthesis loop is routed to a condenser, wherein an overhead stream is withdrawn from the condenser, and wherein at least a portion of the overhead stream is routed as a recycle stream back to the methanol synthesis loop.

12. A process for the production of methanol comprising the following steps:
   (a) providing a source of syngas, wherein the syngas has a first composition parameter $R_1$, and wherein $R_1 > 2$;
   (b) providing a first membrane having a first feed side and a first permeate side, where the first membrane exhibits a selectivity to hydrogen over carbon dioxide of at least about 5, and a selectivity to hydrogen over carbon monoxide of at least about 20;
   (c) passing syngas across the first feed side;
   (d) withdrawing from the first permeate side a hydrogen-rich first permeate stream, wherein the first permeate stream has a second composition parameter $R_2$, and wherein $R_2 > R_1$;
   (e) withdrawing from the first feed side a hydrogen-depleted first residue stream;
   (f) compressing the first residue stream;
   (g) passing the compressed first residue stream to a methanol synthesis loop to produce a condensed methanol product stream;
   (h) withdrawing a purge stream from the methanol synthesis loop to limit the concentration of inerts and excess hydrogen;
   (i) treating the purge stream to decrease its R value and its content of methane and nitrogen, whereby the treated purge stream has a third composition parameter $R_3$, and wherein $R_3 < R_2$; and
   (j) passing the treated purge stream to the methanol synthesis loop.

13. A process in accordance with claim 12, wherein the first membrane exhibits a selectivity to hydrogen over carbon dioxide of at least about 10.

14. A process in accordance with claim 12, wherein the syngas is passed across the first feed side at a temperature within the range of about 50° C. to about 150° C.

15. A process in accordance with claim 12, wherein the first feed side is maintained at a pressure within the range of about 10 bar to about 30 bar.

16. A process in accordance with claim 12, wherein the first permeate side is maintained at a pressure within the range of about 2 bar to about 5 bar.

17. A process in accordance with claim 12, wherein the first residue stream is compressed to a pressure within the range of about 45 bar to about 100 bar before being passed to step (g).

18. A process in accordance with claim 12, wherein step (i) comprises the following sub-steps:
   (I) providing a second membrane having a second feed side and a second permeate side, where the second membrane is selective for carbon dioxide over hydrogen and methane;
   (II) passing the purge stream across the second feed side;
   (III) withdrawing from the second permeate side a carbon dioxide-enriched second permeate stream; and
   (IV) passing the second permeate stream as the treated purge stream to step (j).

19. A process in accordance with claim 18, wherein the second membrane has a selectivity for carbon dioxide over hydrogen of at least about 5.

20. A process in accordance with claim 18, wherein the second membrane has a selectivity for carbon dioxide over methane of at least about 10.

* * * * *